(12) United States Patent
Ensing et al.

(10) Patent No.: US 10,542,884 B2
(45) Date of Patent: Jan. 28, 2020

(54) DETERMINING GLOBAL SHAPE PARAMETERS OF A CORNEA USING A TWO-FOLD FITTING FROM MEASUREMENT DATA TO AN ASPHERIC TORIC SURFACE MODEL

(71) Applicant: Cassini B.V., 's-Gravenhage (NL)

(72) Inventors: Ronald Matijs Ensing, Leiden (NL); Victor Arni De Paz Sicam, Rotterdam (NL)

(73) Assignee: Cassini B.V., 's-Gravenhage (NL)

( * ) Notice: Subject to any disclaimer, the term of this patent is extended or adjusted under 35 U.S.C. 154(b) by 0 days.

(21) Appl. No.: 15/105,104

(22) PCT Filed: Dec. 19, 2014

(86) PCT No.: PCT/NL2014/050892
§ 371 (c)(1),
(2) Date: Jun. 16, 2016

(87) PCT Pub. No.: WO2015/093965
PCT Pub. Date: Jun. 25, 2015

(65) Prior Publication Data
US 2017/0000336 A1     Jan. 5, 2017

(30) Foreign Application Priority Data

Dec. 20, 2013   (NL) .................................... 2012004

(51) Int. Cl.
*A61B 3/107*   (2006.01)
*A61B 3/103*   (2006.01)
*A61B 3/14*    (2006.01)
*A61B 3/00*    (2006.01)

(52) U.S. Cl.
CPC ............ *A61B 3/107* (2013.01); *A61B 3/0025* (2013.01); *A61B 3/1035* (2013.01); *A61B 3/14* (2013.01)

(58) Field of Classification Search
CPC ..... A61B 3/107; A61B 3/0025; A61B 3/1035; A61B 3/14
USPC ...................................................... 351/212
See application file for complete search history.

(56) References Cited

U.S. PATENT DOCUMENTS

2011/0105943 A1   5/2011   De Paz Sicam et al.
2012/0109595 A1   5/2012   Legerton et al.

FOREIGN PATENT DOCUMENTS

WO        2009/056161 A1    5/2009

*Primary Examiner* — Jack Dinh
(74) *Attorney, Agent, or Firm* — Hoffmann & Baron, LLP (57) ABSTRACT

A method of determining global shape parameters of a cornea includes determining a height map of a cornea by: illuminating a cornea of an eye using a stimulator source having a plurality of point sources; capturing a reflected image of the plurality of point sources and determining a position of reflections of the respective plurality of point sources and deriving the height map of the cornea based on a position of the plurality of point sources and the position of the reflections of the respective plurality of point sources; fitting the height map as derived to a toric aspheric model to obtain a global fitting of the corneal surface to the toric aspheric model and; using the global fitting to determine one or more parameters related to an astigmatism of the cornea.

12 Claims, 4 Drawing Sheets

DETERMINING GLOBAL SHAPE PARAMETERS OF A CORNEA USING A TWO-FOLD FITTING FROM MEASUREMENT DATA TO AN ASPHERIC TORIC SURFACE MODEL

CROSS-REFERENCE TO RELATED APPLICATIONS

This application is the National Stage of International Application No. PCT/NL2014/050892 filed Dec. 19, 2014, which claims the benefit of Netherlands Application No. NL 2012004, filed Dec. 20, 2013, the contents of which is incorporated by reference herein.

BACKGROUND

Corneal topographers are currently used to obtain curvature and height data and generate topographic maps of a corneal surface of an eye. Compared to keratometers, corneal topographers enable to provide a more detailed description of the corneal surface, e.g. including local variations over the corneal surface, and whereby data of the central and peripheral parts of the cornea can be obtained.

At present, method have been developed to process the height data as obtained from measurements using a corneal topographer to obtain so-called simK indices, such indices being used to characterize astigmatism. Such simK indices e.g. being:

Rmin (or Ksteep)
Rmax (or Kflat)
Angle of astigmatism

The indices are referred as simK (simulated keratotomy) because the processing of the height data to obtain the astigmatism parameters simulates the operation of a keratometer, which is typically used to characterize astigmatism parameters.

In the known methods to determine the astigmatism parameters, 1-dimensional fits are made along various meridians to determine flattest meridian. This meridian may then be used to determine Kflat, the corresponding angle may be selected as the angle of astigmatism.

For the mentioned method reference can e.g. be made to US 2012/0109595.

A drawback of the known methods to derive global parameters such as astigmatism parameters is that the known methods suffer from a poor repeatability. As a result, when such parameters have been derived, e.g. from 2D corneal height data, an uncertainty may arise whether the derived parameters are sufficiently accurate. In particular, with respect to the angle of astigmatism, a high repeatability is desired because an error of only 10 degrees in the angle of astigmatism would render an astigmatic correction useless.

SUMMARY OF THE INVENTION

It is an object of the present invention to provide in a more accurate calculation of global shape parameters of a cornea. These parameters may refer to the front or the back surface of the cornea.

In accordance with a first aspect of the present invention, there is provided a method of determining global shape parameters of a corneal surface, the method comprising:
determining a height map of the corneal surface by:
   i. Illuminating a cornea of an eye using a stimulator source comprising a plurality of point sources;
   ii. capturing a reflected image of the plurality of point sources and determining a position of reflections of the respective plurality of point sources from the captured reflected image and
   iii. deriving the height map of the corneal surface based on a position of the plurality of point sources and the position of the reflections of the respective plurality of point sources, by performing a surface fitting using a set of global functions;
fitting the height map as derived to a toric aspheric model to obtain a global fitting of the corneal surface to the toric aspheric model and;
using the global fitting to determine one or more parameters related to an astigmatism of the cornea.

The method according to the first aspect of the invention comprises a first step of determining a height map of a corneal surface. In accordance with the present invention, use is made of a stimulator source comprising a plurality of point light sources to in use illuminate the cornea of an eye. In an embodiment, LEDs can be used as light sources. An arrangement of monochrome LEDs may be applied, alternatively, LEDs of different colors may be applied as well. In the latter case, identifying a correspondence between a light source and a reflection of the light source on a reflective image may be facilitated. The step of determining the height map includes illuminating a cornea of an eye using a stimulator source comprising a plurality of point sources, capturing a reflected image of the plurality of light sources and determining a position of reflections of the respective plurality of point sources. Using the position of the point light sources, i.e. the coordinates (x, y, z) and the determined positions of the reflections, i.e. the coordinates (x, y) on the reflected image (e.g. captured by a 2D CCD camera), a corneal height map or surface height can be determined. This can e.g. be done using ray-tracing algorithms.

In an embodiment, the deriving of the height map includes the step of performing a surface fitting using a set of global functions such as Zernike polynomials. Such polynomials are global functions with a comparatively large domain, rendering a reconstruction or fitting using such functions comparatively robust to noise. In this respect, reference can e.g. be made to WO 2009/056161. Using such functions, any devisable shape can be described when a sufficiently high order is selected. There is however a trade-off; when an increasing order is used, an improved accuracy is obtained, but at the cost of diminished repeatability. The use of order 8 has been proven to be a good trade-off in the determination of astigmatism parameters. In general, it can be noted that global functions such as Zernike polynomials prove to be very repeatable and very accurate. As an alternative to the use of Zernike polynomials, the use of Fourier series or spline functions can be mentioned.

Compared to known methods, the height map as determined in the present invention is based on point-to-point information, due to the use of a stimulator source comprising a plurality of point shaped light sources, also referred to a point sources. In known methods, Placido rings are used as a light source. The use of such rings may however result in a severe accuracy loss due to a combination of skew ray errors. Alternative known approaches make use of a time-consuming data acquisition that may result in motion artefacts and as a result in a poor repeatability of the measurements.

In a next step, the method according to the first aspect of the present invention provides in fitting the height map as derived to a toric aspheric model to obtain a global fitting of the corneal surface to the toric aspheric model. Whereas a known approach is to use a number of 1-dimensional fits to derive a parameter of astigmatism, the present invention uses a 2-dimensional fitting of the corneal height data. In particular, the corneal height data is fitted to a toric aspheric model.

This fitting is performed, in a preferred embodiment, in two consecutive fitting steps, i.e. a two-fold fitting is performed. In a first step, the corneal height data, i.e. the measurement data obtained, is used to perform a surface fitting using a set of global functions, to obtain a height map. The height map thus derived is a mathematical model describing the corneal height by a combination (e.g. a weighted combination) of global functions such as Zernike polynomials, Fourier series or spline functions. In a next step, the height map as determined is fitted to a toric aspheric model by performing a 2-dimensional fitting.

It has been observed, by means of clinical tests, that such an approach results in an improved repeatability over the known methods, without a loss of accuracy. According to the inventors, the improved repeatability and high accuracy of the method according to the invention can be attributed to the combination of the use of point-to-point information (by using the above described stimulator source) and the fitting to a toric aspheric (i.e. a 2-dimensional) model.

In a next step, the method according to the first aspect of the invention comprises the step of using the global fitting to determine one or more parameters related to an astigmatism of the cornea. Once a fitting of the height data onto a toric aspheric model has been established, the model can be used to determine one or more parameters defining or describing an astigmatism of the cornea. Such parameters may e.g. include Ksteep, Kflat and form factor. Ksteep is in general used to denote the steepest meridian of the cornea, whereas Kflat is used to denote the flattest meridian. The angle corresponding to the flattest meridian is referred to as the angle of astigmatism. The form factor (k) or, equivalently, the eccentricity (e) indicates to what extend the corneal surface is spherical, hyperbolical, parabola or elliptical and affects spherical aberration.

In an embodiment of the present invention, the step of performing the surface fitting using a set of global functions of the corneal height data to obtain the height map, or the global fitting of the height map as derived to the toric aspheric model, is performed using a least squares fitting. Such a least square fitting may e.g. include minimizing a distance norm.

As an example of such a norm, an Euclidean distance norm, e.g. determined in a direction parallel to the optical axis may be applied. Alternatively, a tangential distance norm, whereby the Euclidean distance is determined in a direction perpendicular to a tangent of the surface, i.e. the surface represented by the set of global functions.

According to a second aspect of the invention, there is provided a corneal topographer comprising:
- a stimulator source comprising a plurality of point sources for, in use, illuminating a target surface comprising a corneal surface of an eye;
- an image target configured to capture a reflected image of the plurality of point sources reflected from the target surface; and
- a computational unit configured to:
  i. determine a height map of the corneal surface based on a position of the plurality of point sources and a position of the reflections of the respective plurality of point sources on the captured reflected image;
  ii. fitting the height map as derived to a toric aspheric model to obtain a global fitting of the corneal surface to the toric aspheric model and;
  iii. using the global fitting to determine one or more parameters related to an astigmatism of the cornea.

The corneal topographer according to second aspect of the present invention comprises a stimulator source that is configured to illuminate, during use, a cornea of an eye with a pattern of light provided by a plurality of light sources, such as LEDs. The topographer further comprises an image target configured to capture a reflected image of the plurality of light sources (also referred to as point sources), reflected off of the cornea. In an embodiment, the image target can comprise a camera system, e.g. including a CCD camera or the like.

The corneal topographer according to the invention further comprises a computational unit for processing the image data as obtained from the image target. Such a computational unit may e.g. comprises a microprocessor or the like to process the image data. The image data can e.g. be provided to an input terminal of the computational unit for processing. In accordance with the present invention, the computational unit is configured to determine a height map of the cornea based on a position of the plurality of point sources and a position of the reflections of the respective plurality of point sources on the reflected image. In a embodiment, determining such a height map involves performing a surface and surface normal vector fitting using a set of Zernike polynomials. In order to determine the height map, the computational unit makes use of the coordinates (x, y, z) of the point sources, and the determined coordinates (x, y) of the reflections of the point sources on the image target, e.g. a 2D CCD camera.

The computational unit is further configured to fit the height map as derived to a toric aspheric model to obtain a global fitting of the corneal surface to the toric aspheric model and; using the global fitting to determine one or more parameters related to an astigmatism of the cornea.

In an embodiment, the corneal topographer may further comprise an output terminal for outputting the one or more parameters in any suitable format. As an example, the parameters may be outputted as numerical values or may be outputted as a graphical representation of e.g. the Kflat and Ksteep orientations or positions.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE INVENTION

Figure 1:
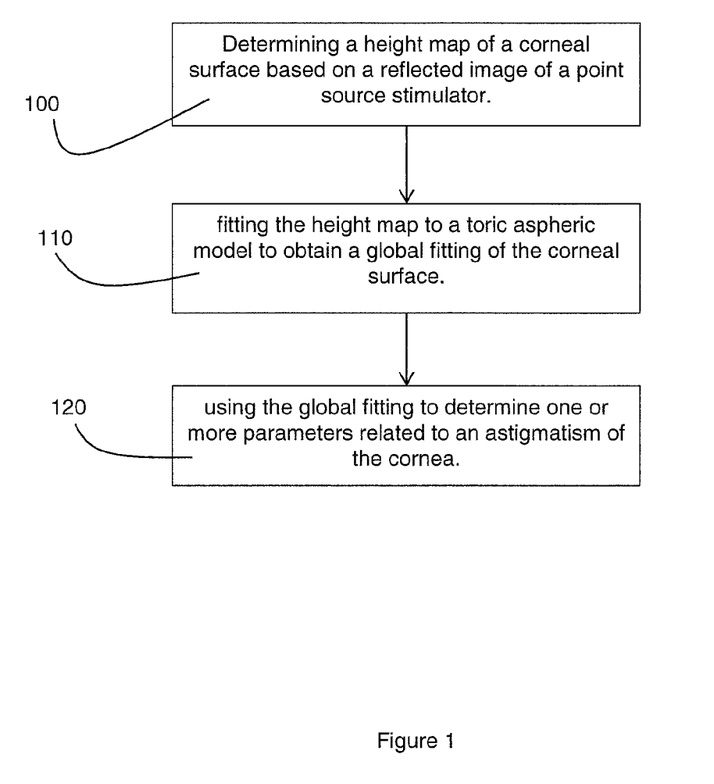
FIG. 1 schematically depicts a flow chart of an embodiment of the method according to the present invention.

FIG. 1 schematically shows a flow chart of an embodiment of the method according to the present invention. The method as shown comprises a first step 100 of determining a height map representing a corneal surface. In accordance with the present invention, the height map is established based on measurement data obtained by illuminating a corneal surface with a stimulator source that comprises point sources, also referred to as a point source stimulator. Within the present invention, the feature 'point source' is used to denote a light source providing a comparatively small, point-like source of illumination, in contrast to e.g. Placido rings having an area-type of illumination. In a preferred embodiment, the height map is derived by performing a surface fitting using a set of global functions such as Zernike polynomials, Fourier series or spline functions.

Using point-like illumination sources enables to provide a more accurate determination of the corneal surface as represented by a height map. As an example of point sources, LEDs can be mentioned. As alternative, a laser-type light source may be considered, whereby a laser beam is distributed into a plurality of point sources using optical fibers. In a second step 110, the height map as derived in the first step 100 is fitted to a toric aspheric model to obtain a global fitting of the corneal surface to such a 2D toric aspheric model. By using a global model, i.e. a 2D model that is fitted to the corneal surface, instead of a number of 1-dimensional fits to derive the astigmatism parameters, it has been observed that the repeatability of the results is significantly improved. It is understood that measurement errors or errors made during the determination of the height map are more averaged out when a 2-dimensional model is used, compared to when a 1-dimensional model is used. As such, the global fitting using the toric aspheric model, which is a 2-dimensional fitting, is less susceptible or less influenced by local errors compared to a (combination of) 1-dimensional fitting. As a result, the repeatability of the results is improved.

In a third step 120, the method according to the first aspect of the invention provides in using the global fitting to the toric aspheric model to determine one or more parameters related to an astigmatism of the cornea.

As an example, when a toric aspheric model is fitted to the height map of the cornea, the parameters describing the toric aspheric model can be used to e.g. determine the steepest and the flattest meridian. Yet another parameter as can be derived from the global fitting is form factor (k) or, equivalently, the eccentricity (e) indicates to what extend the corneal surface is spherical, hyperbolical, parabola or elliptical and affects spherical aberration.

Figure 2:
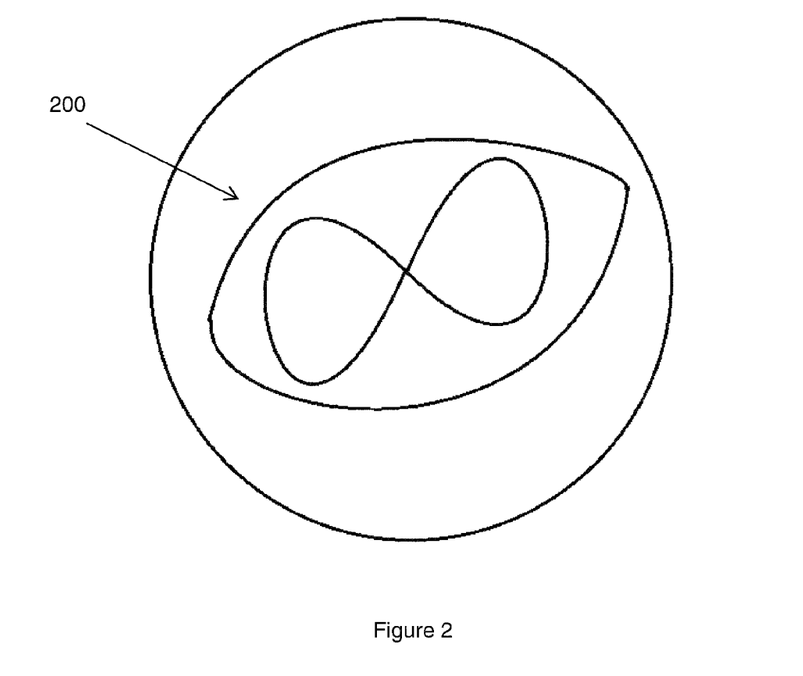
FIG. 2 schematically depicts a height profile of the cornea of an eye.

FIG. 2 schematically shows a height profile 200 of the cornea of an eye. Such height profile or height map may e.g. be determined using a corneal topographer according to the present invention, whereby reflections of a stimulator source are used.

The following describes how the global fitting of the height map may be obtained. In general, a aspheric surface can be described by equation 1:

$$x^2+y^2-2Rz+kz^2 \quad (1)$$

with z the corneal height, x and y the corresponding lateral positions, R the radius of curvature and k the form factor. The mathematical method as describe makes use of matrix equations, therefore the 2D arrays for height (z), position (x) and position (y) can be reshaped to vector arrays in order to use matrix equations. Furthermore, because the aim is to find two radii of curvature, because a toric model for the fitting of the height map or height data (z), the constant R in equation 1 may be replaced by (a vectorised form of) the model for the toric radius of curvature map:

$$R=R_2-(R_2-R_1)\cos(\alpha-\theta)^2 \quad (2)$$

Using trigonometric identities this can be expanded as:

$$R=R_2-(R_2-R_1)(\cos(\theta)\cos(\alpha)+\sin(\theta)\sin(\alpha))^2 \quad (3)$$

With $\alpha$ the angle of astigmatism and $\theta$ the axis of the reference system.

Expanding equation 3 further:

$$R=R_2-(R_2-R_1)(\cos(\theta)^2 \cos(\alpha)^2 + 2\cos(\theta)\cos(\alpha)\sin(\theta)\sin(\alpha)+\sin(\theta)^2 \sin(\alpha)^2) \quad (4)$$

Substituting the x and y coordinates by:

$$R = R_2 - (R_2-R_1)\left(\frac{x^2}{x^2+y^2}\cos(\alpha)^2 + \frac{2xy}{x^2+y^2}\cos(\alpha)\sin(\alpha) + \frac{y^2}{x^2+y^2}\sin(\alpha)^2\right) \quad (5)$$

Now substituting R in equation (1) with the above equation (5) for R:

$$x^2+y^2 - 2\left[R_2 - (R_2-R_1)\left(\frac{x^2}{x^2+y^2}\cos(\alpha)^2 + \frac{2xy}{x^2+y^2}\cos(\alpha)\sin(\alpha) + \frac{y^2}{x^2+y^2}\sin(\alpha)^2\right)\right]z + kz^2 = 0 \quad (6)$$

Multiplying sides of the equation with $x^2+y^2$ to get:

$$(x^2+y^2)^2 - 2\left[R_2 - (R_2-R_1)\left(\frac{x^2}{x^2+y^2}\cos(\alpha)^2 + \frac{2xy}{x^2+y^2}\cos(\alpha)\sin(\alpha) + \frac{y^2}{x^2+y^2}\sin(\alpha)^2\right)\right](x^2+y^2)z + k(x^2+y^2)z^2 = 0 \quad (7)$$

Cancelling out numerator and denominator results in:

$$(x^2+y^2)^2-2[R_2(x^2+y^2)-(R_2-R_1)(x^2 \cos(\alpha)^2+2xy \cos(\alpha)\sin(\alpha)+y^2 \sin(\alpha)^2)]z+k(x^2+y^2)z^2=0 \quad (8)$$

In equation (8), x,y,z are known and $R_1$, $R_2$, $\alpha$ and k are the parameters describing the toric aspheric model. In accordance with an embodiment, equation (8) is reshaped in the form of a matrix multiplication:

$$A=BC \quad (9)$$

when equation 8 is written in this form, the parameters $R_1$, $R_2$, $\alpha$ and k can be found using a least squares fit. Matrix A contains constant parts of equation (8), B is a matrix that contains the dependent part and C is a matrix of coefficients in which the parameters $R_1$, $R_2$, a and k are present. If equation 8 is drafted in this form, one can calculate the coefficients by a multiplication of the pseudo-inverse matrix B with A, which is a least squares fit:

$$B^{-1}A=C \quad (10)$$

The left part of the equation has no coefficients $(x^2+y^2)^2$, so this can be considered the constant matrix A.

$$A=(x^2+y^2)^2 \quad (11)$$

The matrix B then becomes:

$$B=((x^2+y^2)z\ z\ x^2 zxyz y^2 z) \quad (12)$$

The unknown coefficients are therefore given by $$C = \begin{pmatrix} -k \\ 2R_2 - 2(R_2 - R_1)\cos(\alpha)^2 \\ 4(R_2 - R_1)\sin(\alpha)\cos(\alpha) \\ 2R_2 - 2(R_2 - R_1)\sin(\alpha)^2 \end{pmatrix} \quad (13)$$

From the numerical values of C the parameters $R_1$, $R_2$, $\alpha$ and k can be calculated:

$$\begin{pmatrix} -k \\ 2R_2 - 2(R_2 - R_1)\cos(\alpha)^2 \\ 4(R_2 - R_1)\sin(\alpha)\cos(\alpha) \\ 2R_2 - 2(R_2 - R_1)\sin(\alpha)^2 \end{pmatrix} = \begin{pmatrix} C(1) \\ C(2) \\ C(3) \\ C(4) \end{pmatrix} \quad (14)$$

Given the vector array approach as mentioned, matrix A e.g. has 1 column and a number of rows that is equal to the number of points n on which height is calculated (depending on the implementation, n may e.g. be in a range of 5000 to 50000, typically in the range of 20000 to 30000). Matrix B has four columns and n rows and matrix C has 1 column and four rows.

To summarize, equation 8 can be recasted in matrix equation 9 with A, B and C given by equations 11, 12 and 13 respectively.

When the numerical values of matrix C are established, the parameters $R_1$, $R_2$, $\alpha$ and k can be determined by inverting equation 14, resulting in the parameters being described as a function of the coefficients of matrix C:

$$\begin{pmatrix} k \\ R_1 \\ \alpha \\ R_2 \end{pmatrix} = \begin{pmatrix} -C(1) \\ -\frac{1}{4}\sqrt{\frac{C(3)^2 + (C(4) - C(2))^2}{4}} \\ a\sin\left(\frac{C(3)}{2\left(\frac{C(3) + C(4)}{4}\right)}\right) \\ \left(\frac{C(2) + C(4)}{4} + \frac{1}{4}\sqrt{\frac{C(3)^2 + (C(4) - C(2))^2}{4}}\right) \end{pmatrix} \quad (15)$$

As can be seen, the result for $\alpha$ is degenerate. There are two solutions that satisfy the third row of equation 15. These are given by:

$$\alpha = a\sin\left(\frac{C(3)}{2\left(\frac{C(3) + C(4)}{4}\right)}\right) \text{ or} \quad (16)$$

$$\alpha = 180 - a\sin\left(\frac{C(3)}{2\left(\frac{C(3) + C(4)}{4}\right)}\right)$$

In order to get the correct one, the following check can be performed by filling in the solutions for $\alpha$ in the original equation, whereby the a that satisfies $$2R_2 - 2(R_2 - R_1)\cos(\alpha)^2 = C(2) \quad (17)$$

is the angle $\alpha$ we are looking for.

As a convention, the angle of astigmatism will be a value between 0 and 180 degrees. Therefore, if the calculation results in an angle outside this domain, they are given in terms of the identical angle between 0 and 180. This means that the modulo operation may be performed on the a of equation 17. The angle of astigmatism that results from the algorithm is a mod 180.

Using the described algorithm, the parameters $R_1$, $R_2$, $\alpha$ and k can thus be calculated with high precision from the x,y,z, array describing the corneal height data or height map.

Figure 3:
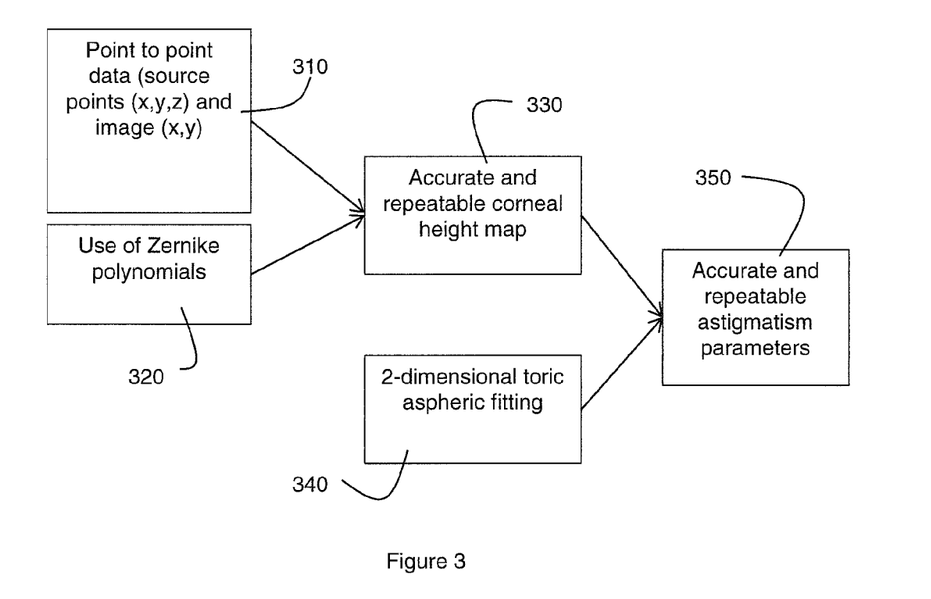
FIG. 3 schematically depicts a flow chart of a preferred embodiment of the method according to the present invention.

In FIG. 3, a flow chart of a preferred embodiment of the present invention is schematically shown:

A point-to-point measurement 310 of a corneal surface form the basis of the calculations. In particular, the coordinates (x,y) of the reflections of the point sources of the stimulator on an image target such as a 2D CCD camera, and the coordinates (x,y,z) of the physical point source locations in space are used. Based on these coordinates, a mathematical model of the corneal surface height, referred to as the corneal height map 330, is derived by performing a first fitting step, the first fitting step involving a surface fitting using a set of global functions. In a preferred embodiment, a set of Zernike polynomials 320 is used as a set of global functions. As a default, Zernike polynomials up to order 8 are applied. In general, the Zernike order can be varied depending on the practical usage. For order 8, 45 coefficients are estimated using a least squares fit on both the corneal surface normal vectors and the height data itself. This fit can be performed in an iterative manner to obtain the coefficients that best describe the cornea.

Increasing the Zernike order results in a required estimation of more coefficients. In theory, a better accuracy would be obtained with increasing Zernike order. However, the total error may increase at a certain increase of the Zernike order, because of an increased sensitivity to noise with an increasing number of coefficients. Order 8 has been found and proved to be an optimum choice.

As a result of the combining of the point-to-point measurement 310 and the use of Zernike polynomials 320, the height map obtained by using this method has proved to have an increased accuracy and repeatability compared to the state of the art. This is due to the fact that:

in known arrangements, placido rings are used instead of point to point information. The use of such rings may result in a severe accuracy loss as a combination of skew ray errors and edge detection errors.

In other known arrangements, a time-consuming data acquisition is used that may result in motion induced artefacts and as a result in a poor repeatability of the measurements.

When the accurate and repeatable corneal height map 330 is established, it is used to obtain a global fitting of a 2-dimensional toric aspheric model 340 to the corneal surface. This can e.g. be done by solving the matrix equation 9 as mentioned above. As a result, accurate and repeatable astigmatism parameters 350 can be obtained.

As an alternative to solving the matrix equation 9, a second fitting step, e.g. using a least square fitting may be applied to fit the corneal height map 330 to the 2-dimensional toric aspheric model.

The inventors of the method as described have in particular observed that fitting the two-dimensional toric aspheric model to a corneal height map which is obtained by a Zernike polynomial fitting to point-to-point corneal height data results in a highly repeatable and accurate axis of astigmatism estimation. By applying a corneal height map as calculated in the preferred embodiment, i.e. by applying a Zernike polynomial fitting to point to point corneal height data, the final result, i.e. the determined astigmatism parameters, is unprecedented.

As an alternative to the use of Zernike polynomials, the following options are worth mentioning:

Fourier series. These are also global functions, like Zernike polynomials. Similar to the use of Zernike polynomials, any shape can be described, provided that a sufficiently high order is selected. As a difference, it can be that Fourier series are defined on an infinite domain, whereas Zernike's are defined in a circular domain. Since a corneal outline resembles a circle and the Zernike polynomials resembles the shapes that are present in optical systems such as the cornea, see e.g. FIG. 2, it may be advantageous to use Zernike polynomials over Fourier series.

Spline functions. The use of spline functions does not actually provide in a fitting, but rather provide an interpolation. This means that the splines pass exactly trough the measurement points. This may result in a more accurate height map, but most likely at a high cost in terms of repeatability.

As mentioned above, the 2-dimensional fitting of the toric aspheric model to the corneal height map can be realized using a least squares fitting. As alternatives, the following options are worth mentioning:

RANSAC or RANdom SAmple Consensus, which is an iterative method to estimate parameters of a mathematical model from a set of measurements which may contain outliers.

Minimum Absolute Deviations.

Figure 4:
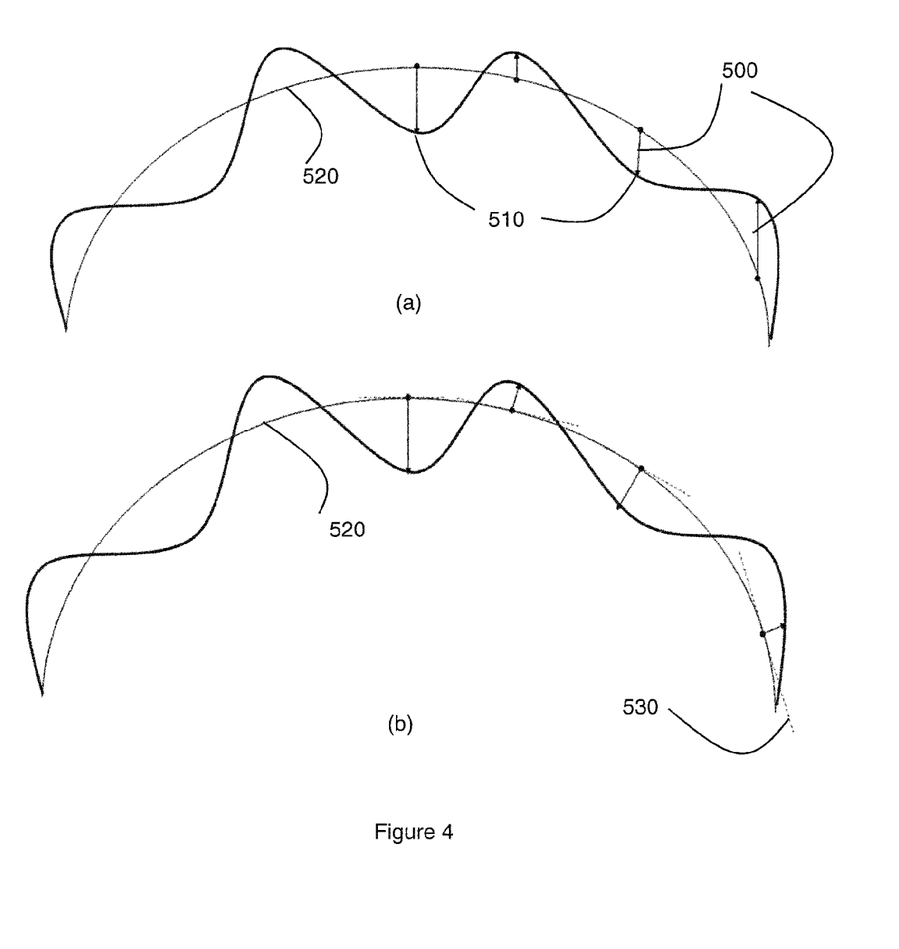
FIG. 4 schematically depicts two distance norms which can be applied to perform a least squares fitting in an embodiment of the present invention.

In an embodiment of the present invention, the step of performing the surface fitting using a set of global functions of the corneal height data (i.e. the point to point corneal height data) to obtain the height map, or the global fitting of the height map as derived to the toric aspheric model, is performed using a least squares fitting. Such a least square fitting may e.g. include minimizing a distance norm. FIG. 4 schematically shows an implementation of an Euclidean distance norm (FIG. 4*a*), whereby the distance 500 between corneal height data points 510 and a target surface 520 is minimized, the distance e.g. being determined in a specific direction, e.g. in a direction parallel to the optical axis may be applied.

Alternatively, a tangential distance norm may be applied, whereby the Euclidean distance is determined in a direction perpendicular to a tangent 530 of the surface 520, i.e. the surface represented by the set of global functions.

As alternatives to the aforementioned toric aspheric model, the following can be mentioned:

An alternative model to the toric aspheric model could e.g. be a Gaussian model in which theta is estimated. However, when using such model, there is no estimation made of astigmatism. When using Gaussians, one could use a mixture of Gaussians to model toric aspheric parameters. However, this model is expected to perform poorly.

With respect to the use of a toric aspheric model, some minor variants or variations could be mentioned. Referring to the asphericity as applied in the model as described, it can be mentioned that this asphericity is assumed to radially symmetric. As an alternative, the asphericity could be assumed to be radially non-symmetric, see e.g. Kiely et al., Optica Acta, 1982, Vol. 29, No. 8, 1027-1040.

Figure 5:
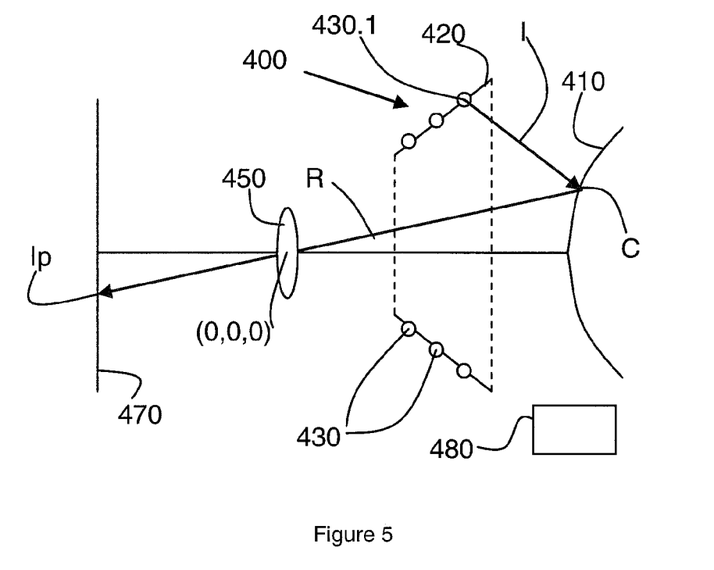
FIG. 5 schematically depicts a corneal topographer according to an embodiment of the present invention.

The methods as discussed above may advantageously be implemented in a corneal topographer according to the present invention. FIG. 5 schematically shows such a topographer. In FIG. 5, an embodiment of the corneal topographer according to the present invention is schematically shown. The embodiment schematically shows a stimulator source 400 arranged to project a plurality of light rays onto a corneal surface 410. The stimulator 400 may e.g. have a conical shaped or a hemispherical shaped surface 220 whereby a plurality of the source points are arranged on this surface 420 for projecting the plurality of light rays onto the corneal surface 410. In an embodiment, the source points can be provided by mounting LEDs 430, optionally of different color, onto the surface 420. As an alternative, the source points can consist of end-points of fiber optics arranged to emit rays of light towards the corneal surface 410. As schematically shown, an incident ray of light I, emitted by source point (Sp) 430.1 (having coordinates (Xs, Ys, Zs)) intersects the corneal surface 410 (at corneal intersection point C (having coordinates (Xc, Yc, Zc)) and results in a reflected ray of light R towards a lens 450 of an image target, e.g. a camera system such as a CCD camera for recording the corneal reflection. The reflected ray of light R is subsequently receive by a camera plane 470 of the image target resulting in an image point (Ip) having coordinates (Xi, Yi, Zi). The topographer according to the present invention further comprises a computational unit 480, e.g. a computer, or microprocessor or the like for processing the captured images and construct, based on the captured image, a mathematical representation of the corneal surface 410. In particular, in accordance with the present invention, the computational unit 480 is configured to:

i. determine a height map of the corneal surface 410 based on a position of the plurality of point sources (e.g. on the surface 420) and a position of the reflections of the respective plurality of point sources on the captured reflected image (470), by performing a surface fitting using a set of global functions;

ii. fitting the height map as derived to a toric aspheric model to obtain a global fitting of the corneal surface 410 to the toric aspheric model and;

iii. using the global fitting to determine one or more parameters related to an astigmatism of the cornea.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. In this respect, it should be noted that the cited dimensions are only indicative for good understanding and are not restricted to the scope of the invention.

Further, the terms and phrases used herein are not intended to be limiting, but rather, to provide an understandable description of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language, not excluding other elements or steps). Any reference signs in the claims should not be construed as limiting the scope of the claims or the invention.

The mere fact that certain measures are recited in mutually different dependent claims does not indicate that a combination of these measures cannot be used to advantage.

The invention claimed is:

1. A method of determining global shape parameters of a corneal surface, the method comprising:
   determining, in a first step, a height map of the corneal surface by:
   i. illuminating a cornea of an eye using a stimulator source comprising a plurality of point sources;
   ii. capturing a reflected image of the plurality of point sources and determining a position of reflections of the respective plurality of point sources from the captured reflected image and
   iii. deriving the height map of the corneal surface based on a position of the plurality of point sources and the position of the reflections of the respective plurality of point sources, by performing a surface fitting using a set of global functions;
   fitting, in a second step subsequent to the first step, the height map as derived in the first step to a toric aspheric model to obtain a global fitting of the corneal surface to the toric aspheric model and;
   using, in a third step, the global fitting obtained in the second step to determine one or more parameters related to an astigmatism of the cornea.

2. The method according to claim 1, wherein the step of performing a surface fitting includes using a set of Zernike polynomials as the set of global functions.

3. The method according to claim 2, wherein the set of Zernike polynomials includes polynomials up to the $8^{th}$ order.

4. The method according to claim 1, wherein the step of deriving the height map involves performing the surface fitting and a surface normal vector fitting using a set of Zernike polynomials.

5. The method according to claim 1, wherein the one or more parameters include Ksteep, Kflat and form factor.

6. The method according to claim 1, wherein the toric aspheric model is described as:

$$x^2+y^2-2Rz+kz^2 \quad R=R_2-(R_2-R_1)\cos(\alpha-\theta)^2$$

whereby:
z=a corneal height at position (x,y), R=a radius of curvature and k=a form factor.

7. The method according claim 1, wherein the step of fitting the height map as derived to the toric aspheric model or the step of performing the surface fitting using the set of global functions is performed using a least squares fitting.

8. The method according to claim 7, wherein the least squares fitting includes minimizing a distance norm.

9. The method according claim 1, wherein the step of fitting the height map as derived to a toric aspheric model is performed using RANSAC or Minimum Absolute Deviations.

10. A corneal topographer comprising:
    a stimulator source comprising a plurality of point sources for, in use, illuminating a target surface comprising a corneal surface of an eye;
    an image target configured to capture a reflected image of the plurality of point sources reflected from the target surface; and
    a computational unit configured to:
    i. determine, in a first step, a height map of the corneal surface based on a position of the plurality of point sources and a position of the reflections of the respective plurality of point sources on the captured reflected image, by performing a surface fitting using a set of global functions;
    ii. fitting, in a second step subsequent to the first step, the height map as derived in the first step to a toric aspheric model to obtain a global fitting of the corneal surface to the toric aspheric model; and
    iii. using, in a third step, the global fitting obtained in the second step to determine one or more parameters related to an astigmatism of the cornea;
    wherein the computational unit is configured to perform the method according to claim 1.

11. A corneal topographer comprising:
    a stimulator source comprising a plurality of point sources for, in use, illuminating a target surface comprising a corneal surface of an eye;
    an image target configured to capture a reflected image of the plurality of point sources reflected from the target surface; and
    a computational unit configured to:
    i. determine, in a first step, a height map of the corneal surface based on a position of the plurality of point sources and a position of the reflections of the respective plurality of point sources on the captured reflected image, by performing a surface fitting using a set of global functions;
    ii. fitting, in a second step subsequent to the first step, the height map as derived in the first step to a toric aspheric model to obtain a global fitting of the corneal surface to the toric aspheric model; and
    iii. using, in a third step, the global fitting obtained in the second step to determine one or more parameters related to an astigmatism of the cornea.

12. The corneal topographer according to claim 11, wherein the plurality of point sources comprise LED light sources.

* * * * *